United States Patent [19]
Kasori et al.

[11] Patent Number: 5,872,268
[45] Date of Patent: Feb. 16, 1999

[54] PROCESS FOR PREPARING SALT OF FATTY ACID ESTER OF HYDROXYCARBOXYLIC

[75] Inventors: Yukio Kasori; Tetsuro Yamazaki; Keita Kashiwa, all of Mie, Japan

[73] Assignee: Mitsubishi Chemical Corporation, Tokyo, Japan

[21] Appl. No.: 766,458

[22] Filed: Dec. 12, 1996

[30] Foreign Application Priority Data

Dec. 13, 1995 [JP] Japan ..................................... 7-324402

[51] Int. Cl.$^6$ ..................................................... C07C 51/00
[52] U.S. Cl. ........................... 554/163; 554/165; 554/168
[58] Field of Search ..................................... 554/163, 165, 554/168

[56] References Cited

U.S. PATENT DOCUMENTS 1,927,295  9/1933  Powers .

FOREIGN PATENT DOCUMENTS 0278370  8/1988  European Pat. Off. .
1197012  7/1970  United Kingdom .

*Primary Examiner*—Paul J. Killos
*Attorney, Agent, or Firm*—Sughrue, Mion, Zinn, Macpeak & Seas, PLLC

[57] ABSTRACT

A process for the preparation of a salt of fatty acid ester of hydroxycarboxylic acid, which comprises subjecting a fatty acid ester of lower alcohol and an alkaline metal salt or alkaline earth metal salt of hydroxycarboxylic acid to ester interchange in an organic solvent in the presence of a nonionic or anionic surface active agent and an alkali catalyst. The highly pure salt of fatty acid ester of hydroxycarboxylic acid obtained by the separation and purification of the reaction product exhibits a remarkably excellent surface activating ability as compared with the existing commercial products.

21 Claims, No Drawings

PROCESS FOR PREPARING SALT OF FATTY ACID ESTER OF HYDROXYCARBOXYLIC

FIELD OF THE INVENTION

The present invention relates to a process for the preparation of a salt of a fatty acid ester of hydroxycarboxylic acid, particularly a salt of fatty acid ester of lactic acid, by the reaction of a fatty acid ester of lower alcohol with a salt of hydroxycarboxylic acid.

BACKGROUND OF THE INVENTION

It is known that a salt of a fatty acid ester of hydroxycarboxylic acid such as a salt of a fatty acid ester of lactic acid is useful as an anionic surface active agent for food, cosmetics, detergents, etc. (JP-A-64-6237 and JP-A-4-23900 (The term "JP-A" as used herein means an "unexamined published Japanese patent application")).

Representative processes for the preparation of the aforementioned compound reported so far include a process of subjecting lactic acid and a fatty acid to direct esterification at a temperature of from 100° C. to 250° C. in the presence of an alkali catalyst (U.S. Pat. No. 2,733,252), a process of reacting lactic acid with an acid chloride of a fatty acid (U.S. Pat. No. 2,789,992), etc. The fatty acid ester of lactic acid obtained by such a reaction is normally subjected to alkali neutralization in the form of a reaction mixture to form a salt.

However, the reaction product obtained by the aforementioned processes has a considerable amount of unreacted lactic acid or a fatty acid derived from the starting materials in addition the desired fatty acid ester of lactic acid. Further, by-products such as polylactic acids and fatty acid esters thereof are formed in a large amount. When the aforementioned mixture is subjected to neutralization with an alkali, the fatty acid ester of lactic acid is partly hydrolyzed. As a result, the final product has an extremely low purity. The acid chloride process gives a somewhat enhanced reaction yield of the desired product. However, the cost of the facility required in this process is high due to corrosion problems and thus this process is not necessarily desirable from the industrial standpoint of view.

In the past, no reports have been made with respect to the process of subjecting a salt of hydroxycarboxylic acid and a fatty acid ester of lower alcohol to effect ester interchange in an organic solvent to obtain the corresponding salt of fatty acid ester of hydroxycarboxylic acid.

SUMMARY OF THE INVENTION

According to the studies by the inventors of the present invention, it is clear that such a reaction does not substantially proceed due to the heterogeneity of the system, which is the reason why no reports exist so far. However, if a salt of fatty acid ester of hydroxycarboxylic acid can be produced by the ester interchange between a salt of a hydroxycarboxylic acid and a fatty acid ester (i.e., alcoholysis), the amount of by-products in the reaction product can be reduced in comparison with the aforementioned conventional preparation processes and a highly pure product can be obtained. Further, this process would have an advantage in that the decrease in purity due to hydrolysis can be eliminated because neutralization with an alkali is not necessary.

As a result of extensive studies to accomplish the aforementioned object, the inventors of the present invention found that the ester interchange reaction between an alkaline metal salt or alkaline earth metal salt of hydroxycarboxylic acid (hereinafter referred to as "a salt of hydroxycarboxylic acid") and a fatty acid ester of lower alcohol in an organic solvent in the presence of an alkali catalyst if carried out in the presence of a nonionic or anionic surface active agent, can smoothly proceed to produce the corresponding salt of a fatty acid ester of hydroxycarboxylic acid and that the aforementioned object of the present invention can be achieved thereby.

The gist of the present invention resides in a process for the preparation of a salt of a fatty acid ester of hydroxycarboxylic acid, which comprises subjecting a $C_8$–$C_{24}$ fatty acid ester of lower alcohol and an alkali metal salt or alkaline earth metal salt of hydroxycarboxylic acid to an ester interchange in an organic solvent in the presence of a nonionic or anionic surface active agent and an alkali catalyst. The preparation process of the present invention solves the aforementioned disadvantages of the known processes.

DETAILED DESCRIPTION OF THE INVENTION

Hereinafter, the present invention is further described in detail.

Examples of the fatty acid constituting the fatty acid moiety of the fatty acid ester of lower alcohol to be used in the present invention include saturated or unsaturated fatty acids having 8 to 24 carbon atoms, preferably 10 to 22 carbon atoms (e.g., caprylic acid, capric acid, lauric acid, myristic acid, palmitic acid, stearic acid, behenic acid, oleic acid, erucic acid, elaidic acid, ricinoleic acid) may be used. If necessary, branched chain fatty acids or fatty acids having one or more hydroxyl groups (i.e., hydroxyfatty acids) may be used. As the lower alcohol moiety of the fatty acid ester of lower alcohol to be used in the present invention, a primary alcohol having 1 to 4 carbon atoms (e.g., methanol, ethanol, propanol, butanol) may be used preferably, because of the ease of removal of by-produced alcohol and the availability of raw material. These fatty acid esters of lower alcohol may be used in admixture.

Examples of the salt of hydroxycarboxylic acid to be used in the present invention include lactic acid salts, malic acid salts and tartaric acid salts, and lactic acid salts are particularly preferable. The lactic acid salt can be obtained by the neutralization of lactic acid produced by a fermentation method or synthesis method with an alkali. In general, a highly pure product obtained by the synthesis method is preferable. The type of metal salt is selected depending on the purpose. Examples of the alkali metal include sodium and potassium, and examples of the alkaline earth metal include calcium. In general, potassium is desirable.

The hydroxycarboxylic acid and the fatty acid ester of lower alcohol are charged for reaction in a molar ratio of from 1:1 to 1:5, preferably from 1:1 to 1:3. In other words, the content of the fatty acid ester of lower alcohol is from 1 to 5 mols, preferably from 1 to 3 mols, per 1 mol of the alkali metal salt or alkaline earth metal salt of hydroxycarboyxlic acid. If a surface active agent having one or more hydroxyl groups (e.g., polyhydric alcohol surface active agent) is used, it is preferable that the fatty acid ester of lower alcohol be excessively charged because it partly reacts with the surface active agent.

Examples of the alkali catalyst include carbonic alkali or caustic alkali, preferably a hydroxide or carbonate of an alkaline metal or alkaline earth metal. The hydroxide or carbonate of alkaline metal are preferable and the carbonate of alkali (e.g., potassium carbonate, sodium carbonate) is particularly preferable. The metal moiety of the alkali catalyst is preferably the same as the metal moiety of the salt of hydroxycarboxylic acid to be supplied for the reaction. The amount of the catalyst to be added is from 0.5 to 5 mol %, preferably from 1 to 3 mol % based on the fatty acid ester of lower alcohol.

The surface active agent to be used in the present invention is a nonionic or anionic surface active agent. Examples of the nonionic surface active agent include polyhydric alcohol esters such as glycerol fatty acid esters, organic acid ester derivatives thereof, polyglycerol fatty acid esters, sucrose fatty acid esters, sorbitan fatty acid esters and propylene glycol fatty acid esters; polyoxyethylene ethers or ether esters such as polyoxyethylene alkyl ethers, polyoxyethylene glycerol fatty acid ester, esters polyoxyethylene castor oils, hardened castor oils, polyoxyethylene sorbitol fatty acid esters and polyoxyethylene sorbitan fatty acid esters; nitrogen-containing surface active agents such as fatty acid alkanolamide and polyoxyethylene fatty acid amide; and alkyl glucoside. Examples of the anionic surface active agent include carboxylic acid salts such as fatty acid soap, alkylether carboxylic acid salts and N-acylamino acid salts; sulfonic acid salts such as alkyl and alkylallylsulfonic acid salts, sulfosuccinic acid salts and α-olefinsulfonic acid salts; sulfuric acid ester salts such as alkyl and alkylethersulfuric acid ester salts; and phosphoric acid ester salts. Nonionic surface active agents are preferable, and sucrose fatty acid esters are particularly preferable.

Examples of the fatty acid constituting the fatty acid moiety of the sucrose fatty acid ester generally include saturated or unsaturated fatty acids having 8 to 24 carbon atoms, preferably 10 to 22 carbon atoms. Preferably, it is the same fatty acid constituting the fatty acid moiety of the fatty acid ester of lower alcohol to be supplied for reaction. The average degree of substitution is preferably from 1 to 3, more preferably from 1 to 2 (HLB is normally within the range of from 3 to 16, particularly from 10 to 15). The sucrose fatty acid ester enhances the homogeneity of the reaction system and accelerates the reaction. However, if the average degree of substitution or the HLB of the sucrose fatty acid ester deviates from the above defined range, such effects decrease.

The sucrose molecule has eight hydroxyl groups, and so sucrose fatty acid esters include mono- to octa-substituted ones. The term "average degree of substitution" as used herein is defined as follows.

$$\text{Average degree of substitution} = \frac{1 \times \text{mono} \cdot \text{content}(\%) + \ldots + 8 \times \text{octa} \cdot \text{content}(\%)}{100}$$

For example, the average degree of substitution of the sucrose fatty acid esters may be measured by the following method.

Gel permeation chromatography (GPC) was carried out under the following conditions.
Conditions for measurements
   Apparatus: HLC-8020 manufactured by Tosoh Corporation
   Column: TSKgel G2500HXL×4 (7.8 mm ID×30 cm)+ TSK gurad column HXL-L (6.0 mm ID×4 cm); all manufactured by Tosoh Corporation
   Temperature: 40° C.
   Eluent: THF
   Flow speed: 1.0 ml/min
   Detector: RI
   Sample: 0.1 to 0.5 w/v %, 100 µl The weight ratio of mono- to octa-substituted sucrose fatty acid esters was determined respectively from the percent area of the corresponding peak. The average degree of substitution was calculated according to the following equation.

$$\text{Average degree of substitution} = \sum_{i=1}^{8} (i \times Wi/100)$$

wherein Wi is a weight ratio of the sucrose fatty acid ester having an ester substitution of i to the total weight of the sucrose fatty acid esters The content of the surface active agent to be added is normally from 5 to 50 mol %, preferably from 15 to 35 mol % based on the alkaline metal salt or alkaline earth metal salt of hydroxycarboxylic acid. If the amount of the surface active agent falls below the above defined range, the reaction does not proceed sufficiently. On the contrary, if a polyhydric alcohol surface active agent such as sucrose fatty acid ester is used in a too much amount, the fatty acid ester of lower alcohol which should react with the salt of hydroxycarboxylic acid reacts with the surface active agent, inhibiting the progress of the reaction and lowering the yield of the desired product. When the sucrose fatty acid ester is to be used, it is also possible to add the equivalent amount of sucrose and convert it to a sucrose fatty acid ester in the reaction system.

Examples of the organic solvent to be used in the present invention include a tertiary amine such as trimethylamine, triethylamine, pyridine and N,N-dimethylpiperidine; an amide such as formamide and N,N-dimethylformamide; and a dialkyl sulfoxide such as dimethyl sulfoxide. Dimethyl sulfoxide is particularly preferable. The amount of the organic solvent to be used is normally from 20 to 80% by weight, preferably from 30 to 70% by weight based on the sum of the charged amount of the salt of hydroxycarboxylic acid, fatty acid ester of lower alcohol, alkali catalyst, surface active agent and organic solvent.

The reaction is normally carried out at a temperature of from 60° C. to 150° C., preferably from 80° C. to 120° C. The pressure for the reaction is normally from 13 to 6,700 Pa (0.1 to 50 torr), preferably from 130 to 2,700 Pa (1 to 20 torr). In particular, the reaction is preferably carried out under the conditions at which the solvent boils while distilling off the by-produced alcohol from the reaction system. A condenser or distillation column is connected to the top of the reaction vessel so that the solvent is separated from the by-produced alcohol and then returned to the reaction vessel during the reaction.

The reaction is carried out under substantially water free conditions. The water content of the reaction system in which the reaction materials, alkali catalyst, surface active agent and organic solvent have been completely charged is not more than 0.1% by weight, preferably not more than 0.07% by weight. The water content exceeding 0.1% by weight is not preferable, since the fatty acid ester of lower alcohol used as a starting material is hydrolyzed by the alkali catalyst to form a fatty acid soap, which retards the reaction. In such a case, the reaction system needs to be previously dehydrated. If the water content of the reaction system in which all the materials have been charged is expected to fall below 0.1% by weight, the reaction materials, catalyst, solvent and surface active agent are normally charged in the reaction vessel together, followed by the reaction at a predetermined temperature for a predetermined period of time. In some cases, however, either one or both of the two materials may be continuously supplied into the reaction system. If the water content of the reaction system in which all the materials have been charged is expected to exceed 0.1% by weight, the reaction materials may be charged in the reaction vessel together with the organic solvent in an excess amount as compared with the predetermined amount. Then, the organic solvent may be partly distilled off so that the reaction system is dehydrated until the water content reaches not more than 0.1% by weight, followed by the addition of the alkali catalyst.

After the reaction, the alkali catalyst is normally neutralized with an acid and the solvent is distilled off to recover the desired product. Examples of the acid to be used in the neutralization of the alkali catalyst include organic acids such as formic acid, acetic acid, propionic acid, lactic acid, oxalic acid, succinic acid.,. citric acid, maleic acid, malic acid and organic acid, and lactic acid is particularly preferable. If the alkali catalyst is not subjected to neutralization and the solvent is distilled off while the alkali catalyst remains active, the desired salt of the fatty acid ester of hydroxycarboxylic acid is hydrolyzed, resulting in a low yield.

The salt of the fatty acid ester of hydroxycarboxylic acid obtained according to the present invention may be optionally purified by washing, recrystallization, extraction with a solution or the like to obtain a product having a higher purity. In particular, the salt of fatty acid ester of lactic acid thus purified exhibits a remarkably excellent surface activating ability in a pH range close to neutral, as compared with the existing commercial products.

The present invention will be further described with reference to the following examples, but the present invention should not be construed as being limited thereto. The fatty acid ester of lactic acid in the reaction product was analyzed in accordance with the following method:
(Preparation of sample)

The reaction product obtained by condensing the reaction solution is precisely measured out, and then dissolved in a 20:1 (by volume) mixture of tetrahydrofuran and water. The pH of the solution is then adjusted to 3.0 with dilute sulfuric acid. Then, a solution of 9-anthryl diazomethane (ADAM) (available from Funakoshi K.K.) in a 1:1 (by volume) mixture of methanol and acetone is added. The reaction mixture is then stored in a dark place for 1 hour to effect reaction. In this manner, carboxylic compounds, including a fatty acid ester of lactic acid, in the reaction solution are converted to ADAM ester derivatives.
<Analysis conditions> Determined by high performance liquid chromatography Column: Develosil ODS-5 (4.6 mm$\phi$×250 mm) (available from Nomura Chemical Co., Ltd.)

Column temperature: 35° C.

Mobile phase: acetonitrile

Flow speed: 2.0 ml/min

Detector: Fluorescent detector RF-10A (available from Shimadzu Corp.)

Exciting wavelength: 365 nm

Fluorescent wavelength: 412 nm

In the analysis of ADAM ester derivatives under the aforementioned conditions, the fatty acid ester of lactic acid and the fatty acid are detected in this order. The quantity of the fatty acid ester of lactic acid in the sample can be determined from a calibration curve previously obtained.

EXAMPLE 1

In a reaction vessel equipped with an agitator and a heating jacket, 640 g of potassium lactate, 438 g (15 mol % based on potassium lactate) of a sucrose lauric acid ester having an average degree of substitution of 1.3 (Ryoto Sugar Ester LWA-1570, available from Mitsubishi Chemical Corporation; freeze-dried product having HLB of 15) as a nonionic surface active agent and 3,029 g of DMSO were charged. The solvent was then entirely refluxed at a temperature of 80C under a pressure of 15 torr for 15 minutes, and 1,000 g of DMSO was distilled off to remove water from the reaction system. At this time, the water content of the system was 0.05% by weight. To the reaction system were then added 1,091 g of methyl laurate and 21 g of potassium carbonate. The reaction mixture was then subjected to reaction at a temperature of 90° C. under a pressure of 20 torr with stirring at 500 r.p.m. for 10 hours while boiling DMSO. The percent conversion of potassium lactate was 75%. Then, 55 g (1 equivalent to the catalyst) of a 50% aqueous solution of lactic acid was added to neutralize the catalyst. The pressure was further decreased to distill off DMSO. The quantity of potassium lauroyl lactate in the reaction product determined by high performance liquid chromatography as described above was 59% by weight (yield: 75% based on potassium lactate).

EXAMPLE 2

The reaction procedure of Example 1 was repeated under the same conditions except that 179 g (15 mol % based on potassium lactate) of a potassium laurate was present as an anionic surface active agent instead of sucrose lauric acid ester. As a result, the percent conversion of potassium lactate was 50%. The quantity of potassium lauroyl lactate in the reaction product determined by high performance liquid chromatography as described above was 43% by weight (yield: 75% based on potassium lactate).

EXAMPLE 3

In a reaction vessel equipped with an agitator and a heating jacket, 640 g of potassium lactate, 845 g (25 mol % based on potassium lactate) of a sucrose stearic acid ester having an average degree of substitution of 1.3 (Ryoto Sugar Ester S-1570, available from Mitsubishi Chemical Corporation; HLB: 15) as a nonionic surface active agent and 5,375 g of DMSO were charged. The solvent was then entirely refluxed at a temperature of 80° C. under a pressure of 15 torr for 15 minutes, and 1,000 g of DMSO was distilled off to remove water from the reaction system. At this time, the water content of the system was 0.05% by weight. To the reaction system were then added 2,890 g of methyl stearate and 42 g of potassium carbonate. The reaction mixture was then subjected to reaction at a temperature of 90° C. under a pressure of 20 torr with stirring at 500 r.p.m. for 7 hours while boiling DMSO. When the percent conversion of methyl stearate reached 80%, the pressure was further decreased and the reaction was continued for 3 hours while distilling off DMSO. The final percent conversion of potassium lactate was 98%. After the reaction, 110 g (1 equivalent to the catalyst) of a 50% aqueous solution of lactic acid was added to neutralize the catalyst. The quantity of potassium stearoyl lactate in the reaction product determined by high performance liquid chromatography as described above was 46% by weight (yield: 98% based on potassium lactate).

COMPARATIVE EXAMPLE 1

The reaction procedure of Example 1 was repeated under the same conditions except that the sucrose fatty acid ester was not used. As a result, the reaction solution remained separated. The upper and lower phases were separated from each other, and then each was determined for the quantity of potassium lauroyl lactate. However, no potassium lauroyl lactate was determined. Even when the rotation speed for agitation was raised to 800 r.p.m., almost no reaction was found.

EXAMPLE 4

In a reaction vessel equipped with an agitator and a heating jacket, 640 g of potassium lactate, 507 g (15 mol % based on potassium lactate) of a sucrose stearic acid ester having an average degree of substitution of 1.3 (Ryoto Sugar Ester S-1570, available from Mitsubishi Chemical Corporation; HLB: 15) as a nonionic surface active agent and 3,592 g of DMSO were charged. The solvent was then entirely refluxed at a temperature of 80° C. under a pressure of 15 torr for 15 minutes, and 1,000 g of DMSO was distilled off to remove water from the reaction system. At this time, the water content of the system was 0.03% by weight. To the reaction system were then added 1,445 g of methyl stearate and 21 g of potassium carbonate. The reaction mixture was then subjected to reaction at a temperature of 90° C. under a pressure of 20 torr with stirring at 500 r.p.m. for 10 hours while boiling DMSO. The percent conversion of methyl stearate was 65%. The pressure was further decreased and the reaction was continued for 3 hours while distilling off the solvent. The percent conversion of potassium lactate was 70%. After the reaction, 55 g of a 50% aqueous solution of lactic acid was added to neutralize the catalyst. The quantity of potassium stearoyl lactate in the reaction product determined by high performance liquid chromatography as described above was 54% by weight.

EXAMPLE 5

The reaction procedure of Example 4 was repeated under the same conditions except that 257 g of sucrose was added instead of sucrose stearic acid ester. As a result, the final percent conversion of potassium lactate was 75%. The quantity of potassium stearoyl lactate in the reaction product determined by high performance liquid chromatography as described above was 65% by weight.

EXAMPLE 6

The reaction procedure of Example 4 was repeated under the same conditions except that a sucrose stearic acid ester having an average degree of substitution of 1.5 (Ryoto Sugar Ester S-1170, available from Mitsubishi Chemical Corporation; HLB: 11) was used. As a result, the final percent conversion of potassium lactate was 68%. The quantity of potassium stearoyl lactate in the reaction product determined by high performance liquid chromatography as described above was 52% by weight.

EXAMPLE 7

The reaction procedure of Example 4 was repeated under the same conditions except that a sucrose stearic acid ester having an average degree of substitution of 2.1 (Ryoto Sugar Ester S-570, available from Mitsubishi Chemical Corporation; HLB: 5) was used. As a result, the final percent conversion of potassium lactate was 63%. The quantity of potassium stearoyl lactate in the reaction product determined by high performance liquid chromatography as described above was 45% by weight.

COMPARATIVE EXAMPLE 2

The reaction procedure of Example 4 was repeated under the same conditions except that no sucrose fatty acid ester was used. As a result, the potassium lactate underwent almost no reaction, and the reaction solution remained separated.

EXAMPLE 8

The reaction procedure of Example 1 was repeated under the same conditions except that sodium lactate was used as a starting material and sodium carbonate was used as a catalyst. As a result, the final percent conversion of sodium lactate was 70%. The quantity of sodium stearoyl lactate in the reaction product determined by high performance liquid chromatography as described above was 54% by weight.

COMPARATIVE EXAMPLE 3

The reaction procedure of Example 8 was repeated under the same conditions except that no sucrose fatty acid ester was used. As a result, the potassium lactate underwent almost no reaction, and the reaction solution remained separated.

EXAMPLE 9

The reaction procedure of Example 1 was repeated under the same conditions except that potassium hydroxide was used as a catalyst. As a result, the percent conversion of potassium lactate was 50%. The quantity of potassium lauroyl lactate in the reaction product determined by high performance liquid chromatography as described above was 40% by weight.

EXAMPLE 10

In a reaction vessel equipped with an agitator and a heating jacket, 545 g of calcium lactate, 507 g (15 mol % based on potassium lactate) of a. sucrose stearic acid ester having an average degree of substitution of 1.3 (Ryoto Sugar Ester S-1570, available from Mitsubishi Chemical Corporation; HLB: 15) as a nonionic surface active agent and 3,597 g of DMSO were charged. The solvent was then entirely refluxed at a temperature of 80° C. under a pressure of 15 torr for 15 minutes, and 1,000 g of DMSO was distilled off to remove water from the reaction system. At this time, the water content of the system was 0.03% by weight. To the reaction system were then added 1,445 g of methyl stearate and 21 g of potassium carbonate. The reaction mixture was then subjected to reaction at a temperature of 90° C. under a pressure of 20 torr with stirring at 500 r.p.m. for 10 hours while boiling DMSO. The pressure was further decreased and the reaction was continued for 3 hours while distilling off DMSO. As a result, the final percent conversion of potassium lactate was 30%. The quantity of calcium stearoyl lactate in the reaction product determined by high performance liquid chromatography as described above was 25% by weight.

COMPARATIVE EXAMPLE 4

The reaction procedure of Example 10 was repeated except that no sucrose fatty acid ester was used. As a result, the calcium lactate underwent almost no reaction, and the reaction solution remained separated.

TABLE 1

| | Salt of hydroxycarboxylic acid | Fatty acid ester of lower alcohol | Surface active agent | | | Alkali catalyst | % Conversion of a salt of hydroxycarboxylic acid | Purity of product (wt %) |
|---|---|---|---|---|---|---|---|---|
| | | | Kind | Average degree of substitution | Added amount (%)* | | | |
| Example 1 | Potassium lactate | Methyl laurate | Sucrose lauric acid ester | 1.3 | 15 | Potassium carbonate | 75 | 59 |
| Example 2 | Potassium lactate | Methyl laurate | Potassium laurate | — | 15 | Potassium carbonate | 50 | 43 |
| Example 3 | Potassium lactate | Methyl stearate | Sucrose stearic acid ester | 1.3 | 25 | Potassium carbonate | 98 | 46 |
| Example 4 | Potassium lactate | Methyl stearate | Sucrose stearic acid ester | 1.3 | 15 | Potassium carbonate | 70 | 54 |
| Example 5 | Potassium lactate | Methyl stearate | Sucrose | — | 15 | Potassium carbonate | 75 | 65 |
| Example 6 | Potassium lactate | Methyl stearate | Sucrose stearic acid ester | 1.5 | 15 | Potassium carbonate | 68 | 52 |
| Example 7 | Potassium lactate | Methyl stearate | Sucrose stearic acid ester | 2.1 | 15 | Potassium carbonate | 63 | 45 |
| Example 8 | Sodium lactate | Methyl laurate | Sucrose lauric acid ester | 1.3 | 15 | Sodium carbonate | 70 | 54 |
| Example 9 | Potassium lactate | Methyl laurate | Sucrose lauric acid ester | 1.3 | 15 | Potassium hydroxide | 50 | 40 |
| Example 10 | Calcium lactate | Methyl stearate | Sucrose stearic acid ester | 1.3 | 15 | Potassium carbonate | 30 | 25 |
| Comparative Example 1 | Potassium lactate | Methyl laurate | None | — | 0 | Potassium carbonate | trace | — |
| Comparative Example 2 | Potassium lactate | Methyl stearate | None | — | 0 | Potassium carbonate | trace | — |
| Comparative Example 3 | Sodium lactate | Methyl laurate | None | — | 0 | Sodium carbonate | trace | — |
| Comparative Example 4 | Calcium lactate | Methyl stearate | None | — | 0 | Potassium carbonate | trace | — |

*: The added amount of surface active agent is represented in mol % based on a salt of hydroxycarboxylic acid According to the present invention, the ester interchange between an alkaline metal salt or alkaline earth metal salt of hydroxycarboxylic acid with a fatty acid ester of lower alcohol in the presence of a nonionic or anionic surface active agent and an alkali catalyst makes it possible to produce the corresponding a salt of fatty acid ester of hydroxycarboxylic acid. The highly pure salt of fatty acid ester of hydroxycarboxylic acid obtained by the separation and purification of the reaction product exhibits a remarkably excellent surface activating ability as compared with the existing commercial products.

While the invention has been described in detail and with reference to specific embodiments thereof, it will be apparent to one skilled in the art that various changes and modifications can be made therein without departing from the spirit and scope thereof.

This application is based on Japanese patent application 7-324402, filed on Dec. 13, 1995, incorporated herein by reference.

What is claimed is:

1. A process for the preparation of a salt of fatty acid ester of a hydroxycarboxylic acid, which comprises subjecting a $C_8$–$C_{24}$ fatty acid ester of a lower alcohol and an alkali metal salt or alkaline earth metal salt of the hydroxycarboxylic acid to ester interchange in an organic solvent in the presence of a nonionic or anionic surface active agent and an alkali catalyst.

2. The process according to claim 1, wherein said hydroxycarboxylic acid is lactic acid.

3. The process according to claim 1, wherein said $C_8$–$C_{24}$ fatty acid ester of lower alcohol is a $C_{10}$–$C_{22}$ fatty acid ester of lower alcohol.

4. The process according to claim 1, wherein said surface active agent is a nonionic surface active agent.

5. The process according to claim 4, wherein said nonionic surface active agent is a sucrose $C_8$–$C_2$4 fatty acid ester.

6. The process according to claim 4, wherein said nonionic surface active agent is a sucrose fatty acid ester having an average degree of substitution of from 1 to 3.

7. The process according to claim 1, wherein the content of said surface active agent is from 5 to 50 mol % based on the alkali metal salt or alkaline earth metal salt of lactic acid.

8. The process according to claim 1, wherein the content of said surface active agent is from 15 to 35 mol % based on the alkali metal salt or alkaline earth metal salt of lactic acid.

9. The process according to claim 1, wherein said alkali catalyst is a carbonic alkali or caustic alkali.

10. The process according to claim 9, wherein said alkali catalyst is a hydroxide or carbonate of the alkali metal or alkaline earth metal.

11. The process according to claim 9, wherein said alkali catalyst is a hydroxide or carbonate of the alkali metal.

12. The process according to claim 1, wherein the content of said alkali catalyst is from 0.5 to 5 mol % based on said fatty acid ester of a lower alcohol.

13. The process according to claim 1, wherein the content of said alkali catalyst is from 1 to 3 mol % based on said fatty acid ester of a lower alcohol.

14. The process according to claim 1, wherein said organic solvent is selected from the group consisting of a tertiary amine, an amide or a dialkyl sulfoxide.

15. The process according to claim 1, wherein said alkali metal salt or alkaline earth metal salt of a hydroxycarboxylic acid is potassium lactate.

16. The process according to claim 1, wherein the content of said fatty acid ester of a lower alcohol is from 1 to 5 mols per 1 mol of said alkali metal salt or alkaline earth metal salt of hydroxycarboxylic acid.

17. The process according to claim 1, wherein the content of said fatty acid ester of lower alcohol is from 1 to 3 mols per 1 mol of said alkali metal salt or alkaline earth metal salt of hydroxycarboxylic acid.

18. The process according to claim 1, wherein the temperature for reaction is from 60° C. to 150° C.

19. The process according to claim 1, wherein the pressure for reaction is from 13 Pa to 6,700 Pa.

20. The process according to claim 1, wherein the water content in the reaction system is not more than 0.1% by weight.

21. The process according to claim 18, wherein the temperature for reaction is from 80° C. to 120° C.

* * * * *